(12) United States Patent
Novak Krmpotic et al.

(10) Patent No.: US 10,322,001 B2
(45) Date of Patent: Jun. 18, 2019

(54) IMPLANT HAVING A MULTILAYERED COATING AND A PROCESS FOR PREPARING THEREOF

(75) Inventors: Sasa Novak Krmpotic, Ljubljana (SI); Natasa Drnovsek, Ljubljana (SI); Gregor Murn, Dvor (SI)

(73) Assignee: Institut Jozef Stefan, Ljubljana (SI)

( * ) Notice: Subject to any disclaimer, the term of this patent is extended or adjusted under 35 U.S.C. 154(b) by 337 days.

(21) Appl. No.: 13/811,583

(22) PCT Filed: Apr. 13, 2011

(86) PCT No.: PCT/SI2011/000020
§ 371 (c)(1),
(2), (4) Date: Mar. 5, 2013

(87) PCT Pub. No.: WO2012/011878
PCT Pub. Date: Jan. 26, 2012

(65) Prior Publication Data
US 2013/0190888 A1    Jul. 25, 2013

(30) Foreign Application Priority Data

Jul. 22, 2010   (SI) .................................. 201000217

(51) Int. Cl.
*A61F 2/28*     (2006.01)
*A61L 2/00*     (2006.01)
(Continued)

(52) U.S. Cl.
CPC ................ *A61F 2/28* (2013.01); *A61L 27/06* (2013.01); *A61L 27/306* (2013.01);
(Continued)

(58) Field of Classification Search
CPC .......... A61F 2310/00023; A61F 2/3094; A61F 2002/30968; A61F 2002/30062;
(Continued)

(56) References Cited

U.S. PATENT DOCUMENTS 3,981,736 A * 9/1976 Broemer et al. ................ 501/10
4,904,534 A * 2/1990 Nagai .................. A61C 8/0012
                                                428/457

(Continued)

FOREIGN PATENT DOCUMENTS

JP     070974 A    3/1994
WO     080140 A1   10/2003

OTHER PUBLICATIONS

The International Search Report (Form PCT/ISA/210) and the Written Opinion of the International Searching Authority (Form PCT/ISA/237) in PCT/SI2011/000020 dated Sep. 2, 2011.

(Continued)

*Primary Examiner* — Ann Schillinger
(74) *Attorney, Agent, or Firm* — MacCord Mason PLLC

(57) ABSTRACT

The present invention relates to an implant having a multi-layered coating comprising a porous titanium-based layer on the implant, an optional interface titania layer on and/or in the porous titanium-based layer and a bioactive glass layer on and/or in the porous structure formed by the titanium-based and titania layer(s); as well as to a process for preparing an implant having a multilayered coating.

8 Claims, 1 Drawing Sheet

(51) Int. Cl.
*A61L 27/06* (2006.01)
*A61L 27/30* (2006.01)
*A61L 27/42* (2006.01)

(52) U.S. Cl.
CPC ......... *A61L 27/427* (2013.01); *A61L 2420/08* (2013.01); *A61L 2430/02* (2013.01)

(58) Field of Classification Search
CPC .... A61F 2002/30011; A61F 2250/0023; A61F 2310/00203; A61F 2310/00239; A61F 2310/00329; A61F 2310/00407; A61F 2310/00796; A61F 2310/00928; A61F 2310/00976; A61L 27/48; A61L 24/0094; A61L 24/046; A61L 27/34; A61L 29/085; A61L 17/145; A61L 24/0084; A61L 27/306; A61L 27/04; A61L 27/50; A61L 27/58; A61L 2300/604; A61L 2420/08; A61L 2430/12; A61L 2430/38; A61L 27/06; A61L 27/10; A61L 27/56
USPC .......... 623/11.11, 23.29, 23.5, 23.55, 23.57, 623/23.6, 23.53
See application file for complete search history.

(56) References Cited

U.S. PATENT DOCUMENTS

| | | | |
|---|---|---|---|
| 2001/0018614 A1* | 8/2001 | Bianchi | 623/16.11 |
| 2004/0167633 A1* | 8/2004 | Wen | A61F 2/30767 |
| | | | 623/23.57 |
| 2005/0038498 A1* | 2/2005 | Dubrow | A61L 31/14 |
| | | | 623/1.15 |
| 2008/0187571 A1* | 8/2008 | Clineff et al. | 424/426 |
| 2009/0061387 A1* | 3/2009 | Lomicka | A61C 8/0012 |
| | | | 433/173 |

OTHER PUBLICATIONS

D. L. Wheeler et al.: "Differential Healing Response of Bone Adjacent to Porous Implants Coated with Hydroxyapatite and 45S5 Bioactive Glass," Journal of Biomedical Materials Research, vol. 55, No. 4, 2001, pp. 603-612 [XP000002656823].

M. Takemoto et al.: "Mechanical Properties and Osteoconductivity of Porous Bioactive Titanium," Biomaterials, Elsevier Science Publishers BV., Barking, GB, vol. 26, No. 30, Oct. 1, 2005 (Oct. 1, 2005).

Hyun-Min Kim et al: "Bioactive Macroporous Titanium Surface Layer on Titanium Substrate," Journal of Biomedical Materials Research, vol. 52, No. 3, Dec. 5, 2000 (Dec. 5, 2000) [XP000002656825].

* cited by examiner

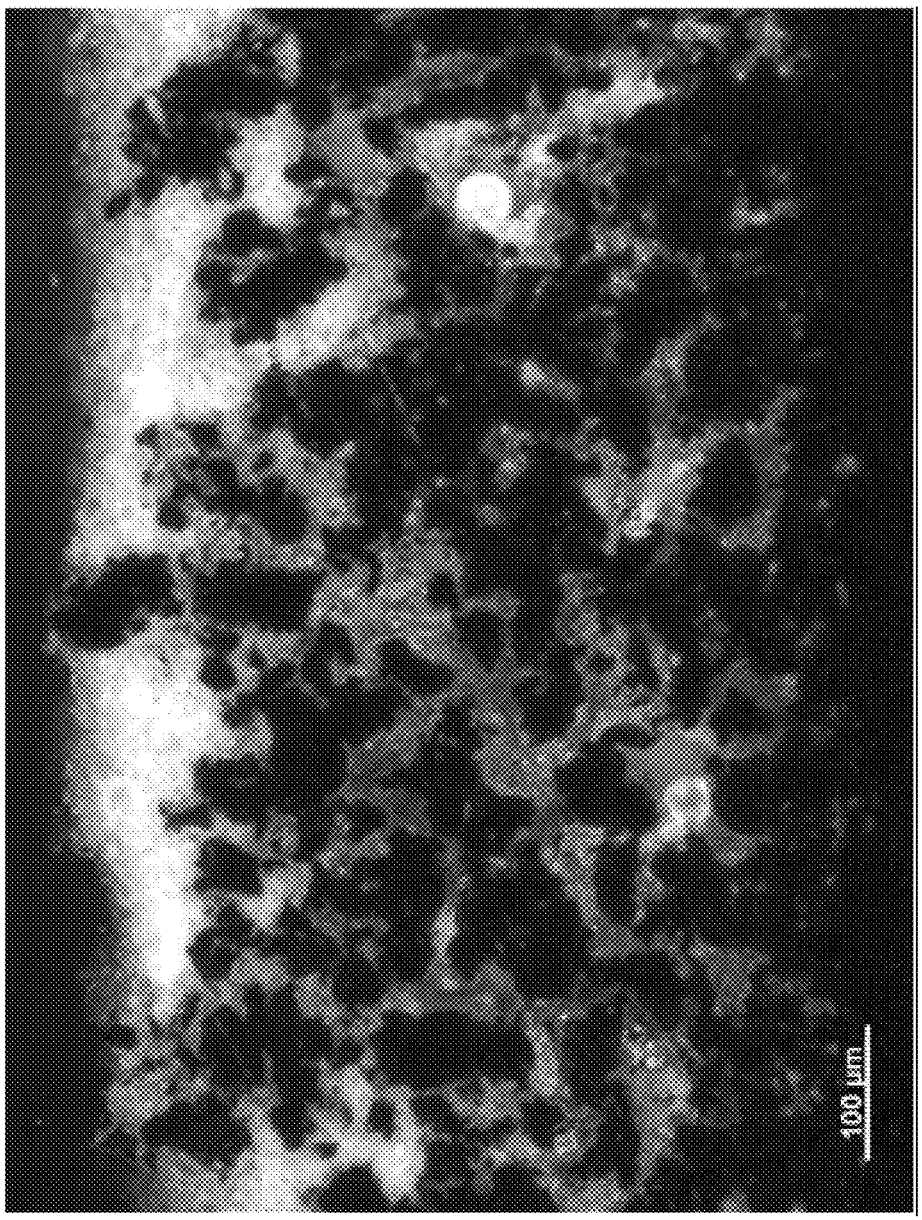

IMPLANT HAVING A MULTILAYERED COATING AND A PROCESS FOR PREPARING THEREOF

This application is a national stage application under 35 U.S.C. § 371 of international application No. PCT/SI2011/000020 filed 13 Apr. 2011, which is incorporated herein by reference in its entirety, and claims priority to Slovenian Application No. P-20100021 filed 22 Jul. 2010, which also is incorporated herein by reference in its entirety.

The present invention relates to an implant having a multilayered coating as well as to a process for preparing an implant having a multilayered coating.

Permanent bone implants are due to the need for sufficient mechanical strength mostly made of metals or alloys. The implants, such as, for example the stem in total hip prosthesis, may be either fixed into the bone by aid of cement or without it. In some specific cases the implant can be screwed into the bone. In comparison with cementless, the cemented implants present higher risk of necrotic damage of the bone mostly associated with heat released during hardening of the cement. In addition, a major drawback is the dependence of prosthesis life-time on durability and strength of the cement. For these reasons cementless implants are preferred over the cemented ones.

A cementless implant is in the body in a direct contact with blood plasma and other surrounding bodily fluids. Therefore, besides the required fracture resistance and suitable stiffness, further suitable surface properties such as bioactivity, biocompatibility, non-toxicity, non-allergenic bodily response, corrosion resistance, hydrophilicity, and also antibacterial properties are desired. None of the existing implants possesses all of these properties.

Besides various ferrous, magnesium-based and Co—Cr alloys used for permanent implants, titanium and titanium alloys have been proved as currently the most acceptable materials for permanent bone implants. However, clinical studies have shown that in a relatively high percentage the metallic implants have to be replaced, most frequently due to unsatisfactory in-growth, infections and loosening.

With the aim of improvement, several techniques of implant surface modification have been proposed. Among them surface structuring is the most widely used. Namely, it has been found that bone cells attach better to a rougher metallic surface than to a smooth one. Several solutions have been presented and used in clinical practice: metallic spheres welded onto the implant surface, sand-blasting, machining, introducing grooves onto the surface and most widely used plasma spraying. Most of this roughening is by mechanical treatment that can introduce impurities, such as unwanted metal atoms or toxic particles, into the implant surface layer.

Although a rough surface promotes cell in-growth, a direct contact of body tissue with a metal surface is not desired due to a potential risk of an allergic response, toxicity of alloying elements or low biocompatibility of metals. For this reason, non-metallic coatings with better bioactivity are preferred. At present, most widely used non-metallic coatings are Ca-phosphate-based coatings, such as hydroxyapatite (HA).

Implant surface modification by application of Ca-phosphate-based coatings can be performed in several ways: ion beam sputtering (U.S. Pat. No. 4,908,030), vacuum plasma sputtering (U.S. Pat. No. 5,543,019), pulse laser deposition, dip-coating followed by thermal or laser treatment, and electrophoretic deposition followed by thermal treatment.

Multilayered Ti precoat, Ti/HA and HA overlayer was formed by plasma deposition in DE 3,516,411.

The use of porous ceramics having interconnected pores as an implantable solid material for bone substitutes has been described (see, e.g., U.S. Pat. No. 5,171,720; Frayssinet et al., Biomaterials, 14, pp. 423-429 (1993);

P. Ducheyne et al (Bioceramics 6, Butterworth-Heinemann, Oxford, 1993, pp. 449-453) describes a double-layer coating including a plasma sprayed HA layer on top of a porous Ti precoat on a Ti substrate. This double-layered coating was shown to outperform a monolithic HA coating in adhesion properties The main disadvantage of these coatings is a weak interfacial bond with the metallic surface that is associated with an increased risk of peeling and solid particles release into the body. Moreover, high temperatures used in thermal treatment can damage the alloy and can change the structural and chemical composition of the coating.

Bioactive glass is a group of highly bioactive silica-rich materials that has been introduced by L. Hench in 1969, see Larry L. Hench, The Story of Bioglass, J. Mater. Sci.: Mater Med (2006) 17:967-978; WO 2007/144662. Later, many researchers followed Hench's guideline toward bioactive glass and glass-ceramic compositions with the aim to further enhance its performance. Bioactive glass is typically (but not necessarily) preferentially amorphous with low crystallinity, since high crystallinity is considered to be detrimental for bioactivity. Hence, the term "bioactive glass" comprises fully amorphous as well as partially crystalline material usually classified as "bioactive glass ceramic."

The main role of bioactive glass is its surface reaction involving ionic dissolution products of critical concentration that stimulate osteoblast cell differentiation and proliferation and also genetically control the osteoblast cell cycle.

In numerous scientific papers that presented the results of the laboratory studies of the effect of composition on the properties of bioactive glasses on their performance under in-vitro as well as in-vivo conditions have confirmed the high potential of this group of materials. It has been shown that it is highly bioactive and that the dissolution rate can be tailored by modification of the composition. However, due to their intrinsic nature, bioactive glasses remain brittle which significantly limits their applications. Consequently, bioactive glasses have been used for defect fillers mainly in dentistry and for facial reconstruction, while due to its insufficient mechanical strength, it has never been used for load-bearing components. For the same reason and in addition due to the great probability of cracking, no successful process for bioactive glass coatings has been proposed.

Depending on their chemical composition, bioactive glasses are soluble in blood plasma providing the essential elements, which stimulate proliferation and division of surrounding bone cells. The main role of bioactive glasses is their surface reaction(s) involving ionic dissolution products of critical concentration. Ion release enhances bone formation through a direct control over genes that regulate cell cycle and stimulate osteogenic precursor cells towards a path of regeneration and self-repair. Several (7) families of genes become activated during the ion release such as; genes encoding various growth factors (including IGF-II and VEG F); transcription factors; cell cycle regulators; apoptosis regulators; DNA synthesis, repair and recombination; cell surface antigens and receptors; signal transduction molecules and extracellular matrix components. Mineralization of the matrix follows soon thereafter and mature osteocyte, encased in a collagen-HCA (hydroxy carbonate apatite), is the final product by 6-12 days in-vitro and in-vivo.

Bioactive glasses dissolve slowly and release the critical concentrations of Si and Ca over many weeks. The initial effect is a proliferation of osteogenic precursor cells. These cells undergo mitosis and lead to an expanded population of mature osteoblast that generate ECM proteins such as type I collagen that mineralizes to form regenerated bone. Critical concentrations of ionic dissolution products (soluble Ca and Si) activate or up-regulate seven families of genes in osteogenic cells. Concentration of soluble Si and Ca at the cell-solution interface is critical for controlling the cell cycle. It is especially important that more osteocalcin is being produced by osteoblast grow on the bioactive material. Osteocalcin is a bone extracellular matrix noncollagenous protein produced by mature osteoblasts and its synthesis correlates with the onset of mineralization. The ionic dissolution products of biologically active Si and Ca released from bioactive glasses stimulate the genes that control osteoblast differentiation as well as proliferation.

The main constituents of a bioactive glass are $SiO_2$ and CaO. It may also contain sodium (Na), phosphorus (P), strontium (Sr), zinc (Zn), magnesium (Mg) and boron (B). Each of these elements usually present in a bioactive glass in the form of oxide has its own function as follows:

Silicon has been proved to have a major influence on bone healing. It stimulates synthesis of collagen and/or its stabilization, and matrix mineralization. Dissolved Si together with Ca ions activates several families of genes synthesizes growth factors that modulate the cell cycle of osteoblast (IGF-II itd). Some papers report that it might interact with serum albumins, fibrinogen and glycosaminoglycans which are components of extracellular matrix. A bioactive glass can comprise silicon at the level of 30 to 95 mole percent (mol %).

Calcium is an indispensable element in every single organism. It is crucial for maintaining cell homeostasis and integrity and it also has an essential roll as a part of secondary messenger system in human body. Calcium stimulates muscle contraction, it promotes cell apoptosis and secretion and it is involved in cell energetic metabolism. Calcium ions released from a bioactive glass are important for the formation of a hydroxyapatite layer on its surface. For the formation of this layer calcium ions from bodily fluids can also be used. The sol-gel bioactive glass can comprise calcium at a level of 0.05 to 40 mol %.

Phosphorus is a key element in all known forms of life. It plays a major role in biological molecules such as DNA and RNA, living cells also use phosphate to transport cellular energy in the form of ATP. This molecule is a key regulator event in cells. Phospholipids are the main structural components of all cellular membranes. Calcium phosphate salts assist in stiffening bones. Phosphorous ions released from a bioactive glass help in formation of hydroxyapatite layer, however they are not necessarily needed in a bioactive glass composition as it is present in bodily fluids. A bioactive glass can comprise phosphorus at a level of 0 to 40 mol %.

Strontium is a bone-seeking element which has various effects on bone metabolism. In particular, strontium has been shown to improve vertebral bone density and reduce osteoporosis. Besides stimulating the division of osteoblast it might also reduce the action of osteoclasts which remove bone tissue mineralized matrix and break up organic compounds in the bone. Strontium is a network modifier. Larger Sr-cation replaces smaller Ca-cation resulting in expansion of the glass network, increased degradability and therefore better bioactivity. Strontium, as antibacterial material, also directly affects on bacterial metabolism. A bioactive glass can comprise strontium at a level of 0 to 30 mol %.

Zinc is another bone-seeking element. It has a potential to diminish the development of fragile bone tissue more than any other element. It also promotes regeneration of collagen fibers and other plasma proteins probably by induction of tRNA synthesis. Zn is also known by its antiseptic effect. It is also well known that addition of zinc to silicate glasses promotes crystallization and consequently improves strength of bioactive glass. It decreases thermal expansion coefficient which is important when bioactive glass is used for coatings. A bioactive glass can comprise zinc at a level of 0 to 30 mol %.

Some grades of bioactive glass also comprise fluorine, for which advantageous as well as disadvantageous effects are reported.

Because of the important interaction between phosphate and magnesium ions, magnesium ions are essential to the basic nucleic acid chemistry of life, and thus are essential to all cells of all known living organisms. Over 300 enzymes require the presence of magnesium ions for their catalytic action. Adult human bodies contain about 24 g of magnesium, with 60% in the skeleton. It is necessary for regulation of body temperature, muscle contraction and action potential. Magnesium deficiency alters calcium metabolism and the hormones that regulate calcium uptake. Magnesium decreases thermal expansion coefficient of bioactive glass. A bioactive glass can comprise magnesium at a level of 0 to 40 mol %.

Boron is a glass former that is not easily crystallized, therefore it is added to a bioactive glass to increase the crystallization temperature. In addition, it interacts with a wide spectrum of biological molecules such as vitamins, carbohydrates, proteins, nucleotides and it is thought to have an important biological function. It is believed that its uptake does not improve individual's health but it was shown that it is beneficial in situations where there is a deficiency of vitamin D and magnesium in food. A bioactive glass can comprise boron at a level of 0 to 40 mol %.

Dissolution of sodium from the glass results in formation of a silica-rich and $CaO-P_2O_5$-rich bilayer and finally the formation of hydroxycarbonate apatite (HCA). The leached $Na^+$ and $Ca^{2+}$ also affect the physiological balance of solution at the interface and modify the local pH. In fact, the alkalinization may promote synthesis and cross-linking of collagen and the formation of hydroxyapatite—a beneficial effect for in vivo bone growth and repair. However, it was already proved that sodium is not beneficial for bioactive glass to be bioactive. Instead of sodium, potassium can be added to bioactive glass composition, it is also a glass modifier and it provides alkaline pH.

Silver is one of those substances that exhibits antibacterial, antifungal, anti-algae or even antiviral properties and as such it has been used as one of only few naturally occurring antibiotics in pre-war and pre-historic time though. Silver as the component of bioactive glass could be therefore used as broad spectrum antibiotic. However, silver is also known as toxic material and therefore its addition to a bioactive glass composition is better to be avoided. It could be replaced by other antimicrobial elements such as Zn, B or Sr.

Other oxides are also possible to be part of the composition if they are needed for some specific bioactive glass property. But same as for silver their addition has to be considered due to other unwanted properties such as toxicity.

Commercially produced bioactive glasses have been prepared by melting the oxides followed by a fast cooling that prevents or minimizes crystallization. Namely, extensive crystallization was assumed after several studies to lower its bioactivity. In the next step, the glass is milled to relatively fine powder. The main drawbacks of this technique are that impurities are introduced during milling and moreover, even after long term intensive milling, it is not possible to prepare nanosized particles and hence thin coatings are not possible to be made. As a result, most of the commercial bioactive glasses are available in the form of powder with a particle size above 90 microns (μm). Another great disadvantage of melt derived bioactive glass is a limited range of compositions where it still exhibits desired bioactivity. It is also available in the form of granules, fibres and plates.

In a more advanced way bioactive glass is prepared by a sol-gel process. As precursors, alkoxides or nitrates are used. Hydrolysis and condensation reactions are catalysed by acidic catalyst or in some cases reaction proceeds without catalyst. Product of the reactions is a gel that has to be ground to get smaller particles. Some of the processes avoid milling by sudden change in pH at the end of the reaction. Most of the known processes use none or acidic catalyst resulting in gel formation where particles are micron sized, while none of them uses basic conditions for both hydrolysis and condensation, i.e., so called precipitation or particulate route.

Several scientific papers report on trials to apply bioactive glass coatings on various substrate materials, such as on hydroxyapatite and other calcium phosphate coatings, alumina, ceramic composites, Co—Cr alloys, as well as on titanium alloys. The main issue addressed has been thermal expansion coefficient mismatch between the coating and the substrate, which was tried to solve by applying a bond coat to compensate for the difference in shrinkage and hence to avoid cracking.

None of the bioactive glass coatings attained the desired adhesion strength, or the adhesion strength was not considered by the authors at all, or the bond coat comprised unwanted elements (for example aluminium).

In summary, the prior art implants showed a slow and unsatisfactory bonding of these implants, especially metallic permanent bone implants, including surface structured implants, with a bone. This was either a consequence of low bioactivity of the metallic substrate, slow and insufficient adsorption of the needed proteins due to hydrophobicity of the metal and great probability of inflammation caused by the bacteria that might be present in surroundings. In addition, in a long term, the released metal ions may represent a major issue due to an allergic bodily response and consequently inflammation.

It is therefore an object of the present invention to provide an implant having a multilayered coating which overcomes the difficulties and disadvantages of the prior art. Especially, an implant shall be provided which is bioactive and biocompatible and provides firm support to bone cells but also provides a region that enables proteins in blood plasma to rapidly attach to enhance osteointegration.

A further object is to provide a process for preparing an implant having a multilayered coating.

The first object is achieved by an implant having a multilayered coating comprising a porous titanium-based layer on the implant, an optional interface titania layer on and/or in the porous titanium-based layer and a bioactive glass layer on and/or in the porous structure formed by the titanium-based and optional titania layer(s).

It is to be understood in the present invention that due to the porous structure of the titanium-based layer any subsequently applied layers may be present on that porous titanium-based layer or even in the porous titanium layer, i.e., deposited in the pores.

In the present invention, the titanium-based layer may be comprised of pure titanium or any titanium alloy.

Preferably, the implant is a metal-based implant, preferably of titanium, titanium alloy, such as Ti6Al4V, Mg alloy, ferrous alloy, Co—Cr alloy or steel.

The porous titanium-based layer preferably has a thickness of about 0.1 to 5 millimeters (mm) and/or a porosity of 15 to 85% and/or pore size of 20-500 μm, preferably 50-200 μm.

The titania layer may have a thickness of at most 5 μm.

In a preferred embodiment a bioactive glass layer has a thickness of at least 2 μm and/or fills the pores substantially completely.

Even preferred, a bioactive glass layer is applied in the form of a powder, the particle size of the bioactive glass powder is below 10 μm, preferably below 1 μm, and/or is at least partially sintered.

In one embodiment a bioactive glass comprises $SiO_2$ and CaO, and optionally one or more oxide selected from $Na_2O$, $K_2O$, SrO, ZnO, MgO, $B_2O_3$, $P_2O_5$, $Ag_2O$, or a fluorine containing compound.

It is preferred that a bioactive glass comprises from 30 to 95 mass percent (mass %) $SiO_2$, 0.05 to 40 mass % CaO, 0 to 30 mass % SrO, 0 to 40 mass % $P_2O_5$, 0 to 30 mass % ZnO, 0 to 40 mass % MgO, 0 to 40 mass % $B_2O_3$ and 0 to 30 mass % $Na_2O$.

In one most preferred embodiment, a titania layer is applied on the titanium-based layer and/or in the pores of the titanium-based layer and/or wherein a bioactive glass layer is applied on the titania layer and/or in the porous structure formed by the titanium-based and optional titania layer(s).

Preferably, the implant is a permanent and/or load-bearing implant.

The second object is achieved by a process for preparing an implant having a multilayered coating comprising the steps:
a) applying a porous titanium-based layer on the implant,
b) optionally applying an interface titania layer on and/or in the porous titanium-based layer, and
c) applying a bioactive glass layer on and/or in the porous structure formed by the titanium-based and optional titania layer(s).

The porous titanium-based layer may be applied by vacuum plasma spray coating, welding of titanium spheres onto the implant or other surface structuring techniques.

The interface titania layer may be applied by hydrothermal treatment of the implant in a titanium-containing solution.

Finally, a bioactive glass layer may be applied by infiltration of bioactive glass powder suspension on and/or into the porous structure, preferably by means of vacuum or pressure, and preferably densifying the bioactive glass by thermal treatment.

In this regard, it is preferred to provide a sol-gel synthesis of a bioactive glass powder with particle size below 10 μm, preferably below 1 μm, calcining the synthesized powder to eliminate carbonaceous remnants, and then introducing the bioactive glass powder in a form of a non-aqueous slurry into the pores of the titanium-based layer and/or in the porous structure formed by the titanium-based and optional titania layer(s), wherein the thickness of a bioactive glass layer is at least 2 μm, preferably at least 10 μm, and/or the pores are substantially completely filled with the powder. An applied bioactive glass powder is then thermally treated (sintered) to densify.

Surprisingly it was found by the present inventors that an implant having a multilayered coating according to the present invention impressively overcomes the disadvantages of the prior art. An implant with a coating is provided which is firmly attached (adhesion strength>25 MPa) especially on permanent load-bearing implants for use in orthopaedic and dental surgery. The coating comprises a porous metallic surface layer (titanium-based) coated with a titania interface layer (optional) and with a glass or glass-ceramic layer. The coating is multifunctional: The porous metallic layer may provide firm support to the bone cells and to the newly formed bone. A bioactive glass top coating is bioactive (in simulated bodily fluid within seven days hydroxyl apatite is formed with a Ca/P ratio of about 1.6), biocompatible (non-cytotoxic) and hydrophilic (contact angle below 20°) that enables the proteins in blood plasma to rapidly attach. It dissolves in bodily fluid by controlled rate, resulting in moderate pH change not exceeding the value of 8 and provides the body with the essential elements for enhanced osteointegration. By aid of involved elements stimulates the bone cells to rapidly grow and spread into the voids in the metallic surface layer and hence to provide a strong bone attachment to the implant. After dissolving a bioactive glass, the titania interface layer lowers, in a preferred embodiment, the release of metallic ions into the body and hence minimizes undesired bodily responses in long-term (the concentration of metal ions decreased for more than 40%).

Bioactive glasses possess, in addition to the clinically proved effect on bone effects healing, also great potential for osseointegration enhancement and can significantly improve the rate of the bone-cells in growth, provide good adhesion of the bone to the implant and hence the long-term performance of permanent implants in load-bearing applications. An essential feature of the inventive implant is that a bioactive glass can be used in such a way to be coated inside the porous surface structure of the titanium and optional titania structure. In a particularly preferred embodiment, the particle size of a bioactive glass is such as to allow incorporation thereof into the pores and can thus properly fill the space inside the pores.

The coating of the inventive implant can be prepared in a multi-step processing, comprising surface structuring by deposition of the porous titanium-based layer; optional hydrothermal treatment to form the titania interface layer; synthesis of bioactive glass powder with small particle size; deposition or infiltration of a bioactive glass into the porous structure; and thermal treatment.

The multilayered and multifunctional coating of the inventive implant combines surface structuring of bone implants, protective coating and bioactive glass coating. This provides the implant with the properties that accelerate osteointegration and improved long-term performance.

The process for preparing an implant having a multilayered coating according to the present invention is substantially based on the ability to utilize a very specific bioactive glass powder which is as such novel and can be prepared by a newly developed method. The newly developed method for production of bioactive glass powder by particulate sol-gel synthesis enables the preparation of powder with well controlled chemical composition and particle size below 10 μm, preferably below 1 μm, that enables the use of the powder for coating the internal surface of the porous metallic coating on implants in which the pore size is between 20-200 μm. A bioactive glass powder can be introduced into the pores by aid of vacuum or pressure infiltration. Thermal treatment provides a bioactive glass of sufficient integrity and a good attachment on a metal. Such coating provides the implant with high bioactivity and enables good cell attachment and proliferation and hence assures better and faster osteointegration.

The process for preparing an implant having a multilayered coating according to the present invention can be summarized with the following main steps:

1. An implant is first coated by a porous titanium-based layer (e.g., by using plasma spray coating, or welding titanium spheres or alloys onto the implant, or other known suitable surface structuring techniques)
2. An optional titania coating is synthesized by hydrothermal treatment of the implant in a titanium-containing solution.
3. A bioactive glass is prepared by a sol-gel technique, preferably a particulate method, followed by calcination.
4. A bioactive glass coating is made by infiltration of a bioactive glass powder suspension (in organic solvent or) into the porous surface layer by aid of vacuum or pressure.
5. The bioactive glass in the pores is densified by thermal treatment.

Ad. 1: Metal implant is preferably coated with 0.1 to 5 mm thick layer of porous titanium-based layer with interconnected pores in size from 20 to 500 μm and porosity from 15 to 85%. The porous metallic coating can be applied by vacuum plasma spray coating of titanium (or alloy) or by welding coarse titanium particles (or spheres) or other technique. The layer must be firmly attached on the substrate.

Ad. 2: Titania coating is preferably synthesized by heating the implant in a solution of titanium ions, the pH of the solution is preferably 3-12, at 120-300° C. for 6 to 96 hours. The process can be as follows:

Titanium ions in the form of titanium or titanium oxide powder or a titanium salt are added to distilled water, which is then pH adjusted to a pH in the range of 3 to 12 by addition of NaOH, KOH, $Ca(OH)_2$, $NH_4OH$ or tetra-alkyl-ammonium hydroxide, citric acid and phosphoric acid. The mixture is put into an autoclave container with an inside wall of titanium or Teflon or other thermally and chemically resistant material. The implant is dipped into the mixture.

The container is tightly sealed and heated at 120-300° C. for 6 to 96 hours and then cooled down to ambient temperature. The hydrothermally treated implant is rinsed and sonicated with water and/or organic solvent.

The as-prepared titania coating is up to 5 μm thick and is preferentially composed of tightly packed anatase grains with pinacoidal (truncated) particles and is firmly attached on the substrate.

Ad. 3: Bioactive glass powder may be prepared by a sol-gel process via particulate route using alkoxides and nitrates as staring precursors and a base as catalyst. Compositions can be two-component: $SiO_2$—CaO, three-component: CaO—$SiO_2$-MxOy, where M is Na, Sr, Zn, Mg, B, P, Ag; or more-component where more than one MxOy is present. An amount of each oxide compound may vary from 30 to 95 mol % for $SiO_2$, from 0.05 to 40 mol % for CaO, from 0 to 30 mol % for SrO, from 0 to 40 mol % for $P_2O_5$, from 0 to 30 mol % for ZnO, from 0 to 40 mol % for MgO and $B_2O_3$ and from 0 to 30 mol % for $Na_2O$ (molar percentage).

The precursors used for sol-gel can be alkoxides and salts. Precursors for $SiO_2$ can be alkoxide, including but not limited to tetraethyl orthosilicate (TEOS) (preferably), tetramethyl orthosilicate (TMOS), methyltriethoxy silicate (MTEOS). For $P_2O_5$ precursors may include but not limited to triethyl phosphate (TEP). For ZnO, SrO and CaO precursors can be in soluble form including nitrates and acetates. For calcium precursors used are preferably salts, including nitrates or acetates. Precursors used for $Na_2O$ may be salts (preferably) or alkoxide. Sols are prepared under basic conditions.

The precursors (alkoxides, salts) are mixed together with 20-95 volume percent (vol %) preferably 50 vol % alkyl alcohol, including but not limited to ethanol (preferably) or methanol. The mixture of all reagents (mixture M1) is then added dropwise to another mixture of organic solvent (alkyl alcohol, including but not limited to ethanol or metanol), water and base, including but not limited to $NH_3$ preferably, tetramethylammonium hydroxide (TMAH), tetrapropylammonium hydroxide (TPAH), NaOH (if Na is part of composition) (mixture M2). Salts are also added if they are not added into the mixture M1. A $H_2O$/orthosilicate (e.g., TEOS) molar ratio is 4-20. The mixture is stirred vigorously during addition of drops of the mixture M1. The pH value of the mixture M2 is carefully kept constant at about pH 10 (9-12) to assure the same conditions for hydrolysis and condensation for the mixture M1 till the end of the process and to avoid possible insoluble calcium hydroxide formation due to too high pH of the mixture M2. If Na is part of a bioactive glass composition and is added in form of Na-alkoxide it is added to the mixture M1 instead to the mixture M2 and the pH during reaction is not altered with another base as alkoxide itself provides high pH.

The sol-gel synthesis can be also performed by mixing precursors without dropping. In this case the mixture M1 (TEOS/TEP, and solvent that is alkyl alcohol, preferably ethanol or methanol) is poured into the mixture M2 ($H_2O$, salts and solvent that is alkyl alcohol, preferably ethanol or methanol). The pH value of the mixture M2 is set to a value from 9.5 to 11, depending on the composition of bioactive glass, exactly on the amount of the calcium salt, which can precipitate as calcium hydroxide at high pH levels. The pH of the mixture is kept above a pH of 9 by addition of the same base previously used for setting the pH of the mixture M2.

Both processes can be done at room or at higher temperature for accelerating the reaction. The reaction mixture is stirred for an hour(h). The obtained powder suspension is dried preferably at 50° C. and then calcined to get rid off residual organics and nitrates, preferably at 600-700° C., depending on a bioactive glass composition.

The produced powder contains 30 to 95 mol % for $SiO_2$, from 0.05 to 40 mol % for CaO, from 0 to 30 mol % for SrO, from 0 to 40 mol % for $P_2O_5$, from 0 to 30 mol % for ZnO, from 0 to 40 mol % for MgO and $B_2O_3$ and from 0 to 30 mol % for $Na_2O$ (molar percentage).

Ad. 4: Bioactive glass powder is infiltrated into the pores of the coating by vacuum infiltration or by pressure infiltration from a non-aqueous powder suspension.

Bioactive glass powder can be also mixed with biopolymer solution. The suspension is then infiltrated into the pores of the metal coating by vacuum infiltration or pressure infiltration.

Ad. 5: The coating is preferably dried and thermally treated at a temperature from 100 to 900° C. depending on a bioactive glass composition.

The invention will now be described in detail with reference to the following examples in view of the drawings wherein FIG. 1 illustrates an optical micrograph of an inventive implant with bioactive glass coating (white) within the porous titanium layer (black regions) on a Ti6Al4V substrate (lower black part).

EXAMPLE 1

Ti6Al4V implant is vacuum plasma sprayed with a 0.5 mm thick layer of porous titanium with a pore size in the range from 20 to 500 μm.

A suspension for $TiO_2$ coating is prepared from 100 milliliters (ml) of distilled water, 1 gram (g) of titanium powder, 0.5 g of $CaF_2$ and 0.1 g of $SiO_2$. Sodium hydroxide, tetra methyl-ammonium hydroxide, phosphoric acid and citric acid are used to adjust pH to 10.

The implant coated with a porous titanium layer is placed in a Teflon vessel, 50% filled with titania suspension. The vessel is put in a steel autoclave, tightly sealed, closed and heated to 200° C. for 48 h. After heating, the system is cooled to a room temperature by self cooling of the furnace. After the container has cooled, the implant is taken out and perfectly cleaned by rinsing with water, repeated sonication in distilled water (10 times for 10 minutes {min}) and sonication in ethanol for 1 h. The implant is then dried in a stream of hot air for 3 h at a temperature of 50° C.

For a bioactive glass with a composition 58 mass % $SiO_2$-30 mass % CaO-8 mass % $P_2O_5$-4 mass % ZnO mass % two mixtures M1 and M2 are prepared. For the mixture M1 43 ml TEOS and 2 ml TEP are dissolved in 43.5 ml EtOH. The mixture is stirred for an hour in a sealed container to avoid contact with moisture. For the mixture M2 17 g calcium nitrate tetrahydrate is completely dissolved in distilled water, then 1.45 g of zinc acetate is added and dissolved, then 216 ml of EtOH and then another 43 ml of distilled water is added. The pH of the mixture M2 is carefully adjusted to 11 by addition of amonium hydroxide. The mixture is stirred for an hour. The mixture M1 is then added to M2 drop by drop during stirring and the pH is kept constant between 10 and 11.

After stirring, the suspension is dried at 60° C. The obtained powder is calcined at 600° C. for 2 h. An ethanol suspension of bioactive glass powder for infiltration is dispersed with an ultrasonic finger.

Ti6Al4V with a porous Ti layer and coated with titania is placed in a vessel equipped with two valves. One serves for evacuation and the other for adding the suspension. The vessel has to be tightly sealed. The suspension is pumped into the coating pores. After bioactive glass addition negative pressure is held for another 1 to 2 min. Samples are then dried at room temperature.

The coating is then sintered in a vacuum furnace at a sintering temperature of 875° C. for 2 h, and with a heating rate 5° C./min and self cooling of the furnace.

EXAMPLE 2

Ti6Al4V implant is coated by welded titanium spheres.

Suspension for TiO2 coating is prepared from 100 ml of distilled water, 1 g of titanium oxide powder, 0.5 g of $CaF_2$ and 0.1 g of $SiO_2$. Ammonia, tetra methyl-ammonium hydroxide, phosphoric acid and citric acid is used to adjust pH to 10.

The implant is placed in a teflon vessel, 50% filled with titania suspension. Vessel is put in a steel autoclave, tightly sealed, closed and heated to 150° C. for 48 hours. After heating, the system is cooled to a room temperature by self cooling of the furnace. After the container has cooled, the implant is taken out and perfectly cleaned by rinsing with water, repeated sonication in distilled water (10 times for 10 min) and sonication in ethanol for 1 h. The implant is then dried in a stream of hot air for 3 hours at temperature 50° C.

Bioactive glass with a composition 53 mass % $SiO_2$-20 mass % CaO-4 mass % $P_2O_5$-23 mass % $Na_2O$ (mass %) is prepared using alkoxide precursor for $Na_2O$. Two mixtures, M1 and M2 are prepared. For the mixture M1 10 ml TEOS and 0.5 ml TEP are dissolved in 13 ml EtOH. Then 2.56 g of sodium ethoxide dissolved in ethanol is added. The mixture is stirred for an hour in a sealed container to avoid contact with moisture. For the mixture M2 4.28 g of calcium nitrate tetrahydrate is completely dissolved in 5 ml of distilled water and then added to 52 ml of ethanol and 10.5 ml of water. The pH of the mixture M2 is carefully adjusted to 11.3 by addition of ammonium hydroxide. Mixture is stirred for an hour. The M1 is then slowly added to the M2 drop by drop during stirring. The pH value of the mixture M2 is in this case kept constant between 10-11 by sodium ethoxide in the mixture M1, therefore the dropping rate of the mixture M1 is regulated according to the pH of M2.

After stirring the suspension is dried at 60° C. The obtained powder is calcined at 600° C. for 2 h. An ethanol suspension of bioactive glass powder for infiltration is dispersed with an ultrasonic finger.

Ti6Al4V with a porous Ti layer and coated with titania is placed in a vessel equipped with two valves. One serves for the evacuation and the other one for adding the suspension. The vessel has to be tightly sealed. Suspension is pumped into the coating pores. After bioactive glass addition negative pressure is held for another 1-2 min. The sample is then dried at 70° C. The coating is sintered in vacuum furnace at a sintering temperature of 810° C. for 2 h and with heating rate 5° C./min and self cooling of the furnace.

EXAMPLE 3

Ti6Al4V implant is coated by a 0.5 mm thick layer of porous titanium by vacuum plasma spray technique.

For a bioactive glass with a composition 70 mass % $SiO_2$-30 mass % CaO mass %, 5.76 g of calcium nitrate tetrahydrate completely dissolved in 6 g of distilled water was added to 95.64 g of EtOH with 16.36 g of $H_2O$. The pH of the mixture was adjusted to 11.3. After half hour of stirring, 12.584 g of TEOS was added. The mixture was heated to 40° C. and stirred for an hour. The pH was controlled with $NH_4OH$ not to drop under 10.

After stirring the suspension is dried at 60° C. The obtained powder is calcined at 600° C. for 2 h.

For infiltration ethanol suspension of bioactive glass powder with 0.2 wt % PEI1800 is prepared. Suspension is dispersed with an ultrasonic finger.

Ti6Al4V with a porous Ti layer and coated with titania is placed in a vessel equipped with two valves. One serves for evacuation and the other for adding the suspension.

The vessel has to be tightly sealed. Suspension is pumped into the coating pores. After bioactive glass addition negative pressure is held for another 1-2 min. The sample is then dried and sintered in vacuum furnace at a sintering temperature 850° C. for 2 h, with heating rate 5° C./min and self cooling of the furnace.

The features disclosed in the foregoing description, in the drawing and in the claims may, both separately and in any combination thereof, be material for realizing the invention in diverse forms thereof.

The invention claimed is:

1. An implant comprising a substrate and a multilayered coating, the multilayered coating comprising a porous titanium-based layer on the substrate; a bioactive glass layer in or on and in the porous titanium-based layer and a titania layer between the porous titanium-based layer and the bioactive glass layer, wherein the bioactive glass layer is impregnated in the pores of the porous titanium-based layer or deposited on the porous titanium-based layer and impregnated in the pores of the porous titanium-based layer with the titania layer as a separate layer between the bioactive glass layer and the porous titanium-based layer.

2. The implant according to the claim 1, wherein the titania layer has a thickness of at most 5 μm.

3. The implant according to the claim 1, wherein the bioactive glass layer has a thickness of at least 1 μm.

4. The implant according to the claim 1, wherein the bioactive glass is applied in the form of a powder suspension and the particle size of the bioactive glass powder is below 10 μm and that the bioactive glass is at least partially sintered and that the bioactive glass is prepared by melting, sol-gel, preferably particulate sol-gel method.

5. The implant according to the claim 1, wherein the bioactive glass comprises $SiO_2$ and CaO and, optionally, one or more oxides selected from $Na_2O$, $K_2O$, SrO, ZnO, MgO, $B_2O_3$, $P_2O_5$, $Ag_2O$, or a fluorine containing compound.

6. The implant according to the claim 1, wherein the bioactive glass comprises from 30 to 95 mol % $SiO_2$ and 0.05 to 40 mol % CaO and, optionally, one or more oxides selected from $Na_2O$, $K_2O$, SrO, ZnO, MgO, $B_2O_3$, $P_2O_5$, $Ag_2O$, or a fluorine containing compound.

7. The implant according to the claim 6, wherein the bioactive glass comprises one or more of 0 to 30 mol % $Na_2O$; 0 to 30 mol. % $K_2O$; 0 to 30 mol % SrO; 0 to 30 mol % ZnO, 0 to 40 mol % MgO; 0 to 40 mol. % $B_2O_3$; 0 to 40 mol % $P_2O_5$; 0 to 5 mol % $Ag_2O$ or any two or more of the preceding.

8. The implant according to the claim 1, wherein the implant comprises one of a permanent implant, a load-bearing implant, or a permanent and load-bearing implant.

* * * * *